United States Patent
Shukla et al.

(10) Patent No.: US 12,387,326 B2
(45) Date of Patent: Aug. 12, 2025

(54) SYSTEM AND METHOD FOR CANCER IDENTIFICATION USING GENERATIVE ADVERSARIAL NETWORKS AND IMAGE ENTROPY

(71) Applicant: Dell Products L.P., Round Rock, TX (US)

(72) Inventors: Ravi Shukla, Bengaluru (IN); John Anthony O'Shea, Rovinka (IE)

(73) Assignee: Dell Products L.P., Round Rock, TX (US)

( * ) Notice: Subject to any disclaimer, the term of this patent is extended or adjusted under 35 U.S.C. 154(b) by 351 days.

(21) Appl. No.: 18/187,726

(22) Filed: Mar. 22, 2023

(65) Prior Publication Data
US 2024/0320820 A1    Sep. 26, 2024

(51) Int. Cl.
| G06T 7/00 | (2017.01) |
| A61B 5/00 | (2006.01) |
| G06T 7/11 | (2017.01) |
| G06T 7/136 | (2017.01) |

(52) U.S. Cl.
CPC .......... *G06T 7/0012* (2013.01); *A61B 5/4842* (2013.01); *G06T 7/11* (2017.01); *G06T 7/136* (2017.01); *G06T 2207/20084* (2013.01); *G06T 2207/30024* (2013.01)

(58) Field of Classification Search
CPC ........ A61B 5/4842; G06T 2207/20084; G06T 2207/30024; G06T 7/0012; G06T 7/11; G06T 7/136
See application file for complete search history.

(56) References Cited

U.S. PATENT DOCUMENTS

2018/0204046 A1 * 7/2018 Bhattacharya ........ G06F 18/217

OTHER PUBLICATIONS

Stéfan van der Walt et al., "scikit-image: image processing in Python" rDistributed under Creative Commons CC-BY 1.0, retrieved at https://doi.org/10.7717/peerj.453, PeerJ 2:e453. Jun. 19, 2014 (18 pages).

* cited by examiner

*Primary Examiner* — Kenny A Cese
(74) *Attorney, Agent, or Firm* — Chamberlain, Hrdlicka, White, Williams & Aughtry; Aly Z. Dossa

(57) ABSTRACT

A prognosis system is programmed to: obtain, from a biomarker image generation service, a set of original biomarker images, generate a set of synthetic images using the set of original biomarker images, perform an entropy calculation on each of the set of synthetic images to obtain a set of entropy images, apply an entropy thresholding on the set of entropy images to obtain a set of threshold images, apply a masking on the set of threshold images to obtain a pair of masked images for each of the set of threshold images, compare each of the pair of masked images using a cosine similarity (CS) value to assign a cancer value to a corresponding threshold image of the set of threshold images, and based on the cancer value, determine a cancer prognosis to each of the synthetic images.

20 Claims, 7 Drawing Sheets

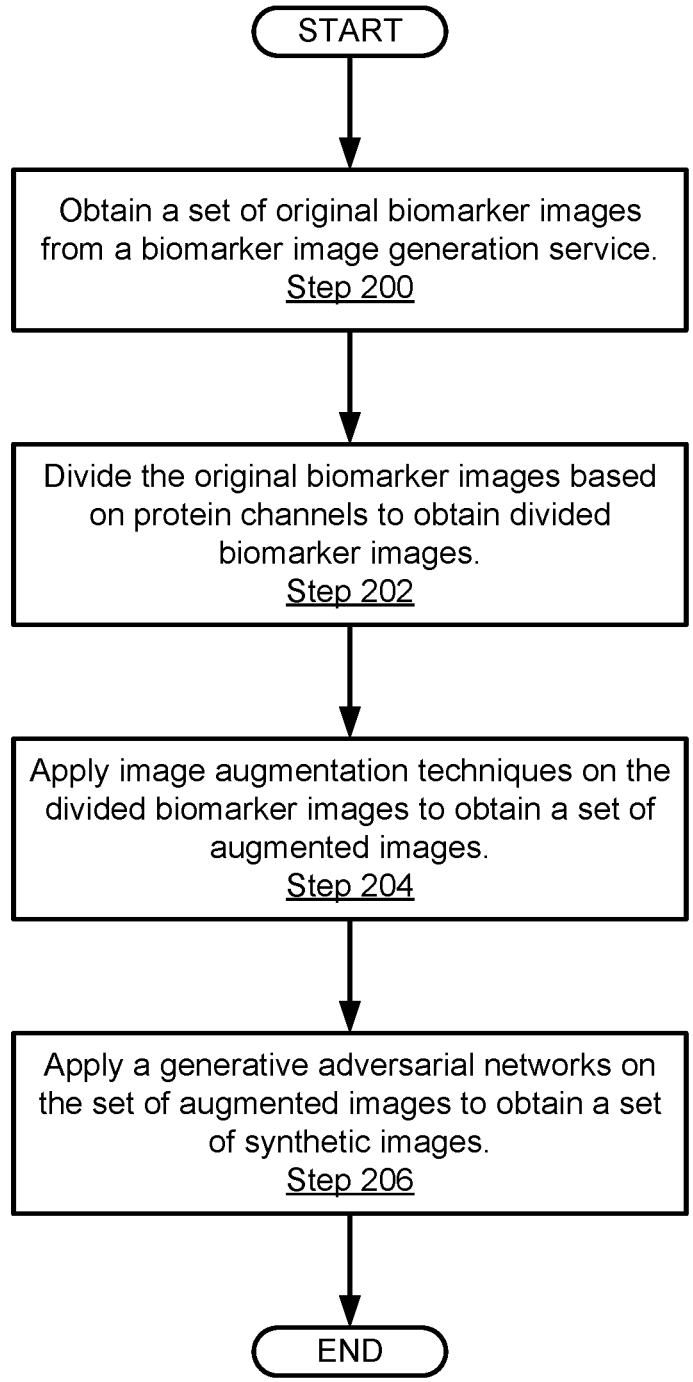
FIG. 2.1

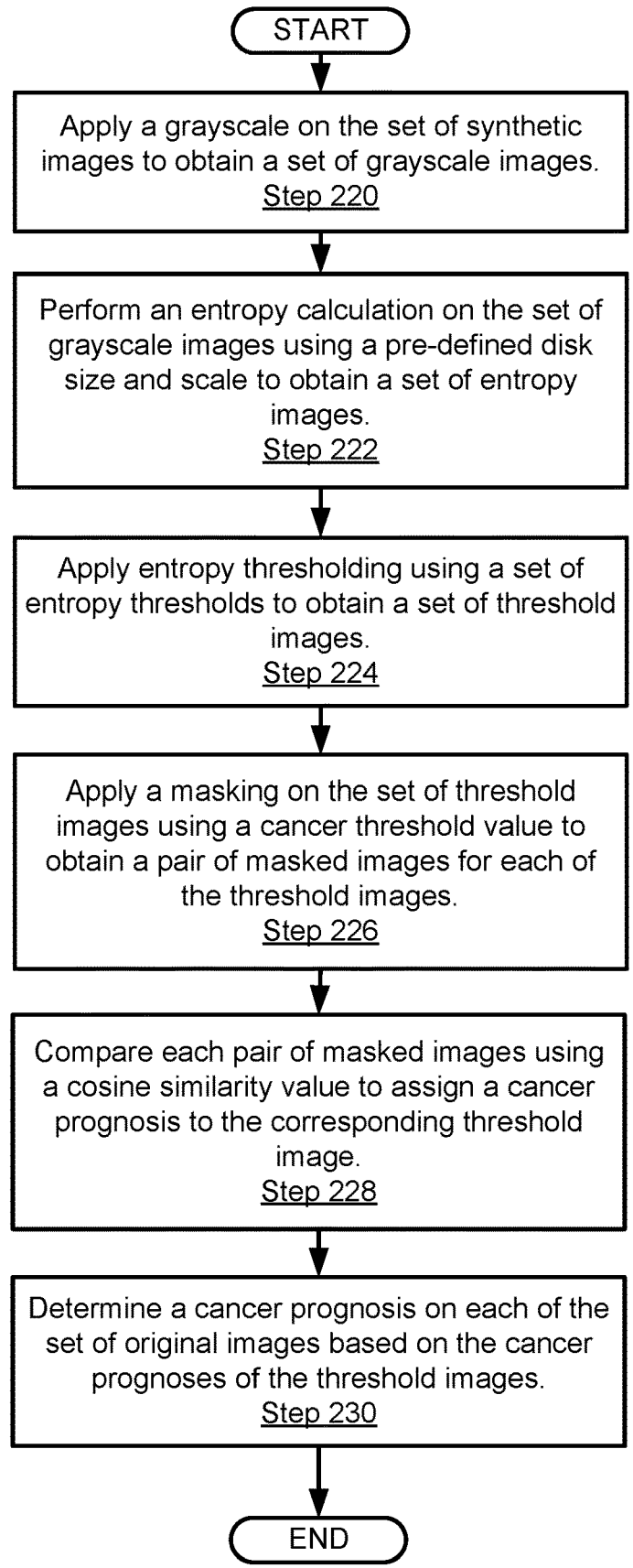
FIG. 2.2

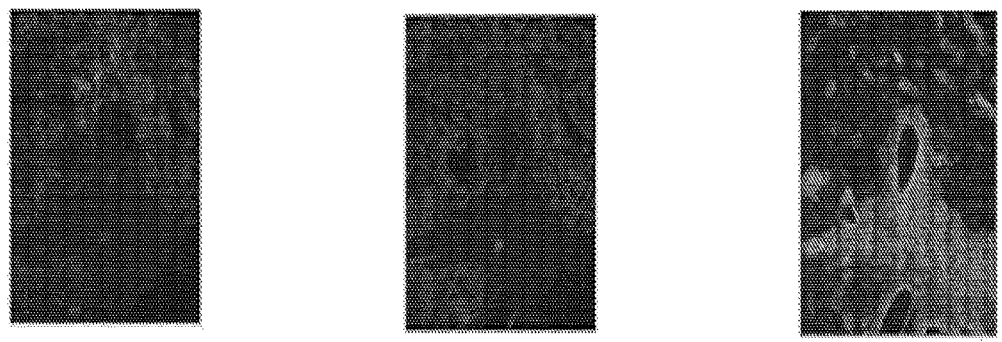
FIG. 3.1
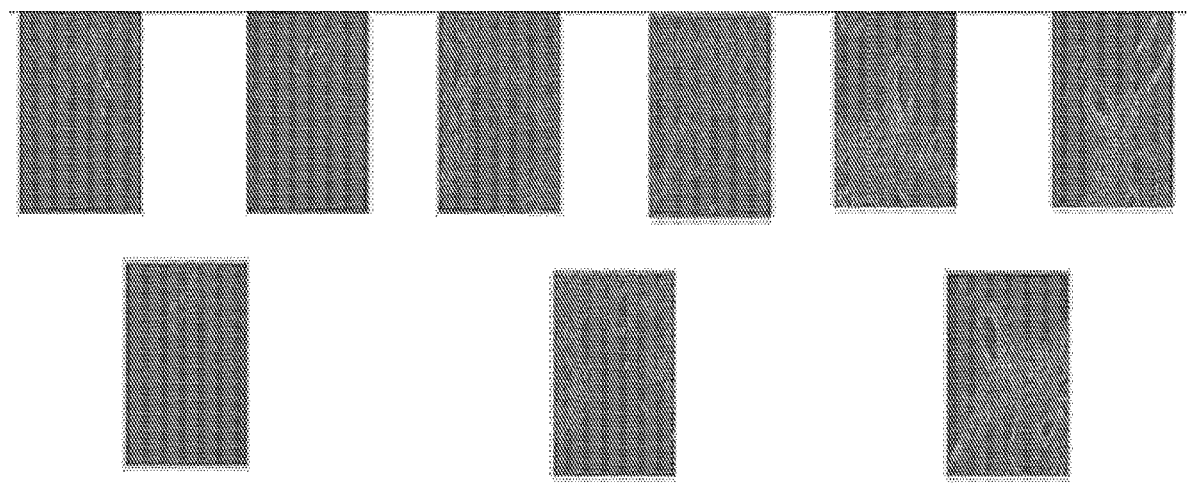
FIG. 3.2

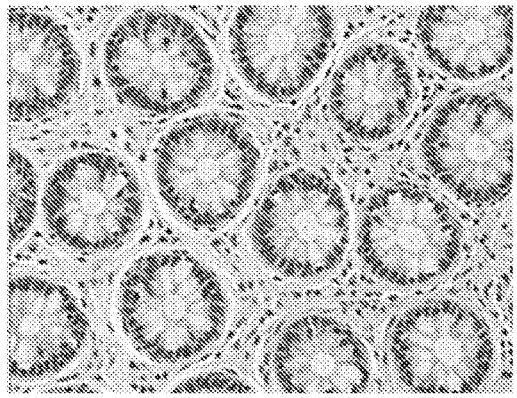
FIG. 3.3
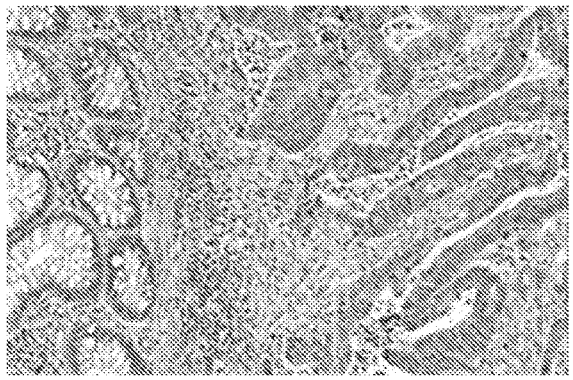
FIG. 3.4
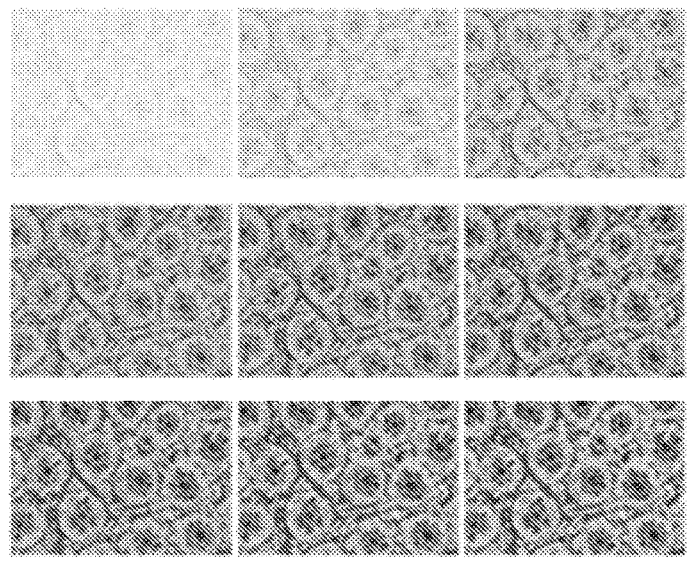
FIG. 3.5

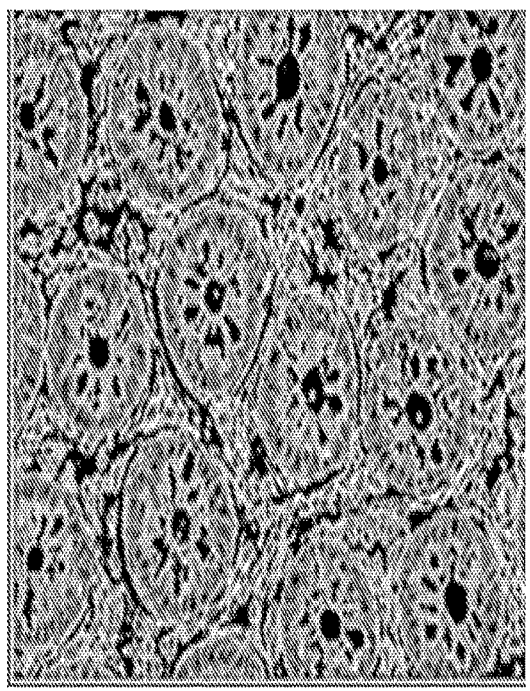
FIG. 3.6
FIG. 3.7

SYSTEM AND METHOD FOR CANCER IDENTIFICATION USING GENERATIVE ADVERSARIAL NETWORKS AND IMAGE ENTROPY

BACKGROUND

Biomarkers may be indicators in the cells of a person that are used to detect signs of abnormal processes such as cancer. The presence of biomarkers may be analyzed to determine how well the normal cells behave to the abnormal processes. The early detection of the abnormal processes using biomarkers may be beneficial for treating illnesses caused by these processes. However, current mechanisms for using biomarkers for detection may be costly.

BRIEF DESCRIPTION OF DRAWINGS

Certain embodiments of the invention will be described with reference to the accompanying drawings. However, the accompanying drawings illustrate only certain aspects or implementations of the invention by way of example, and are not meant to limit the scope of the claims.

FIG. 2.1 shows a flowchart of a method for generating a set of synthetic images in accordance with one or more embodiments of the invention.

FIG. 2.2 shows a flowchart of a method for performing a prognosis using the set of synthetic images in accordance with one or more embodiments of the invention.

FIGS. 3.1-3.7 show example use cases in accordance with one or more embodiments of the invention.

DETAILED DESCRIPTION

Figure 1:
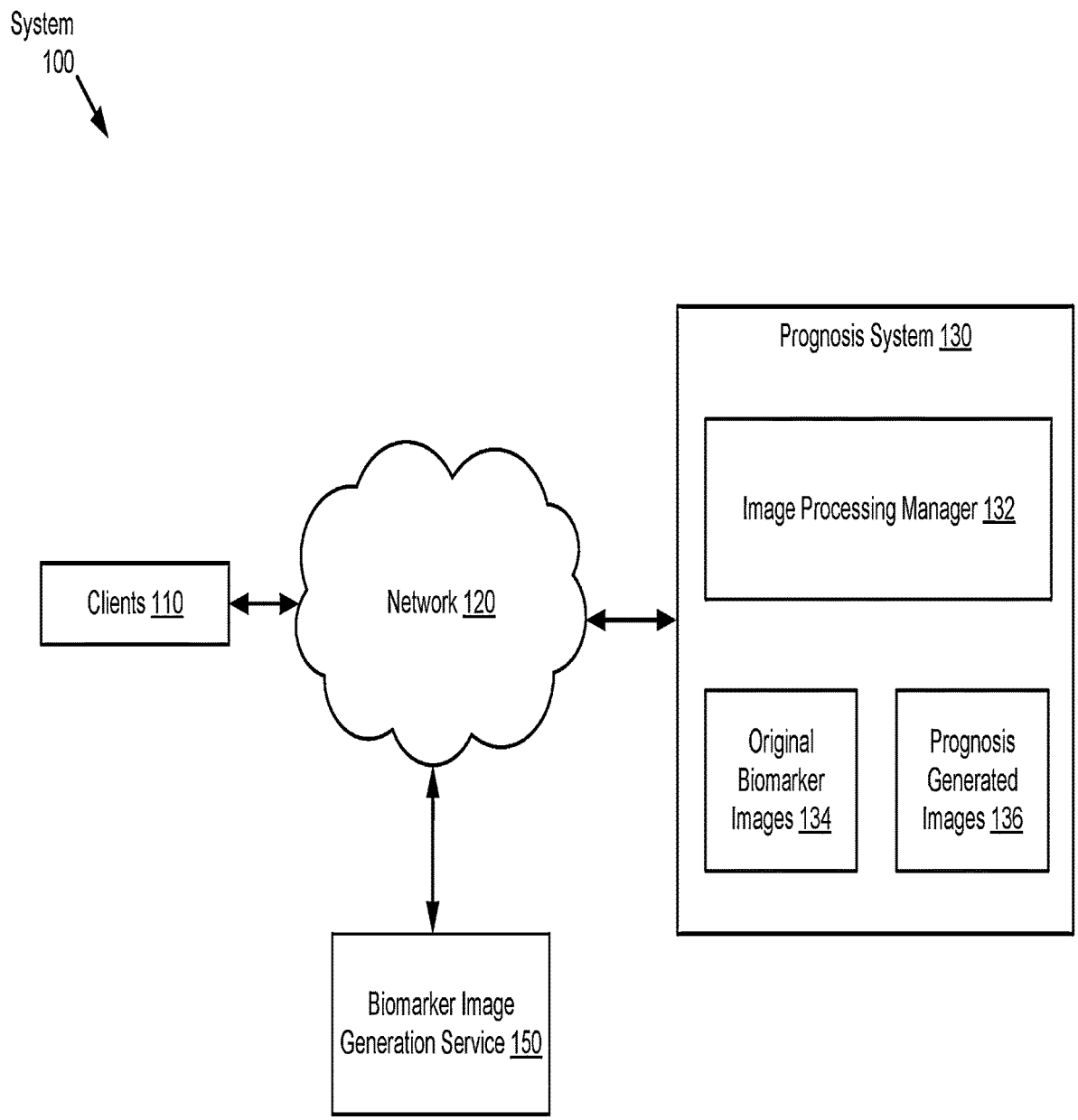
FIG. 1 shows a diagram of a system in accordance with one or more embodiments of the invention.

Specific embodiments of the invention will now be described in detail with reference to the accompanying figures. In the following detailed description of the embodiments of the invention, numerous specific details are set forth in order to provide a more thorough understanding of one or more embodiments of the invention. However, it will be apparent to one of ordinary skill in the art that the one or more embodiments of the invention may be practiced without these specific details. In other instances, well-known features have not been described in detail to avoid unnecessarily complicating the description.

In the following description of the figures, any component described with regard to a figure, in various embodiments of the invention, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the invention, any description of the components of a figure is to be interpreted as an optional embodiment, which may be implemented in addition to, in conjunction with, or in place of the embodiments described with regard to a corresponding like-named component in any other figure.

Throughout this application, elements of figures may be labeled as A to N. As used herein, the aforementioned labeling means that the element may include any number of items, and does not require that the element include the same number of elements as any other item labeled as A to N. For example, a data structure may include a first element labeled as A and a second element labeled as N. This labeling convention means that the data structure may include any number of the elements. A second data structure, also labeled as A to N, may also include any number of elements. The number of elements of the first data structure, and the number of elements of the second data structure, may be the same or different.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

As used herein, the phrase operatively connected, or operative connection, means that there exists between elements/components/devices a direct or indirect connection that allows the elements to interact with one another in some way. For example, the phrase 'operatively connected' may refer to any direct connection (e.g., wired directly between two devices or components) or indirect connection (e.g., wired and/or wireless connections between any number of devices or components connecting the operatively connected devices). Thus, any path through which information may travel may be considered an operative connection.

In general, embodiments of the invention relate to a method and system for performing image processing. Specifically, embodiments disclosed herein include methods and system for processing images of cells to determine whether cancer is present in the cells. Embodiments disclosed herein use generative adversarial networks (GANs) and entropy of images to label images as "cancerous" or "non-cancerous".

In current implementations, methods for detecting cancer in cells may be performed using biomarkers. In one or more embodiments, biomarkers are a biological molecule found in blood, other body fluids, or tissues that are used as a sign of a normal or abnormal process, or of a condition or disease. Within a biomarker, an oncologist may see how well the body responds to a treatment for a disease or condition for example within cancer. The biomarkers may include molecules produced by the body or tumor in a person with cancer. It may be beneficial to test for many types of biomarkers that identify and illustrate the cancer progression status that is aligned to the type of drug inoculated to the patient for treatment of certain types of cancer. For predicting outcome from a biomarker using machine learning (ML), a large number of biomarkers (e.g., cancer-produced molecules, antibodies, etc.) may be required for training the ML model.

One of the common concerns globally is the potential cost of testing for biomarkers. An important distinction, however, regarding the potential cost of testing for biomarkers is between the price for biomarker testing and the price of any related treatments are separate and significantly different. It may be beneficial to properly analyze the progression of certain types of cancer by reducing a required frequency of biomarker testing and/or potentially not requiring the conventional use of biomarker testing. Further, it may be beneficial to improve the analysis of existing images obtained from the biomarker testing.

Embodiments disclosed herein include applying a first process for generating biomarker data artificially across protein channels. The first process may include selecting a dataset of images of a set of biomarkers. For example, an image of a biomarker may be divided into various protein channels. Each image in the dataset may be associated with a protein channel of a biomarker. The first process further includes applying image augmentation techniques on the selected set of images. Examples of image augmentation techniques include, but are not limited to: flipping, rotation, and scaling of the images. The resulting set of images may be applied to a GAN (Generative Adversarial Network) model to obtain a set of processed images.

Embodiments disclosed herein further include applying a second process for categorizing the set of processed images. In the second process, for each synthetic image generated in the first process, the following steps are performed:
  (i) The processed image is converted to a grayscale format.
  (ii) An entropy representation of the image is generated using an entropy disk of a suitable size (an "entropy disk" may refer to a circular structuring element of a radius big enough to capture the variation in an image). In the following example, the entropy disk radius is taken as 6. The image entropy is scaled by dividing each pixel by the maximum value of the pixels to get a scaled entropy image.
  (iii) Threshold plots are generated based on intervals of 0.1 for a range of 0 to 1.0. For each threshold value, the threshold value is applied to each pixel of the scaled image entropy. If the pixel value is less than the threshold value, then the value of the pixel is set to zero; otherwise it stays the same. The resulting set of pixels of a scaled entropy image for a given threshold value is a threshold plot.
  (iv) Masked images are generated using cancer threshold values. As used herein, a cancer threshold value (CTV) is a value of a threshold at which the Threshold plots start resembling the original image. In the example, 0.8 is taken as the CTV as observed across multiple images.
Two Masked Images may be generated as follows:
Mask_CTV_greater-All pixels in a scaled entropy image less than CTV are set to 0.
Mask_CTV_lower-All pixels in a scaled entropy image greater than CTV are set to 0.
The two masked images are converted into their vector representation by applying them to a pre-trained machine vision model and taking its output. In this example, the two vectors are called "Mask_CTV_greater_vector" and "Mask_CTV_lower_vector".
  (v) The cosine similarity (CS) between Mask_CTV_greater_vector and Mask_CTV_lower_vector is calculated. If a CS is less than a predetermined threshold, then the original image is cancerous. In this example, we consider 0.7 as the suitable threshold. That is, for an image with CS<0.7, the output is the image indicates cancer; and for an image with CS>0.7, the output is the image indicates non-cancerous. To explain: A non-cancerous cell is more regular compared to cancerous; Therefore, the mask for a cancerous cell looks similar above and below CTV with a high cosine similarity.

The following describes various embodiments of the invention.

FIG. 1 shows a diagram of a system (100) in accordance with one or more embodiments of the invention. The system (100) includes any number of clients (110), a network (120), a prognosis system (130), and a biomarker image generation service (150). The system (100) may include additional, fewer, and/or different components without departing from the scope of the invention. Each component may be operably connected to any of the other components via any combination of wired and/or wireless connections. Each component illustrated in FIG. 1 is discussed below.

In one or more embodiments, the biomarker image generation service (150), the clients (110), and the prognosis system (130) may be physical or logical devices, as discussed below. In one or more embodiments, the system (100) may include any number of storage devices without departing from the scope of the invention.

While FIG. 1 shows a specific configuration of the system (100), other configurations may be used without departing from the scope of the invention. For example, although the clients (110) and the prognosis system (130) are shown to be operatively connected through the network (120), the clients (110) and the prognosis system (130) may be directly connected, without an intervening network (e.g., 120).

Further, the functioning of the clients (110) and the prognosis system (130) is not dependent upon the functioning and/or existence of the other device(s) in the system (100). Rather, the clients (110) and the prognosis system (130) may function independently, and perform operations locally that do not require communication with other devices. Accordingly, embodiments disclosed herein should not be limited to the configuration of devices and/or components shown in FIG. 1.

In one or more embodiments, the biomarker image generation service (150) is a service that applies biomarker testing on organic tissue. In one or more embodiments of the invention, the biomarker testing includes applying a chemical process to the organic tissue to cause the biomarker to become more visible for the purposes of capturing pictures of the organic tissue with the visible biomarkers. The biomarkers may be biological molecules present in the organic tissue. The presence of biomarkers (or lack thereof) may be detected and analyzed for the purposes of diagnosing the progression of types of cancer (and/or whether a type of cancer is present) in the organic tissue. Other services may be provided by the biomarker image generation service (150) without departing from the invention.

The application of the biomarker testing on the organic tissue may be documented using images of the biomarkers. For example, a set of original biomarker images may be generated. The set of original biomarker images (134) may be provided to the prognosis system (130).

Figure 4:
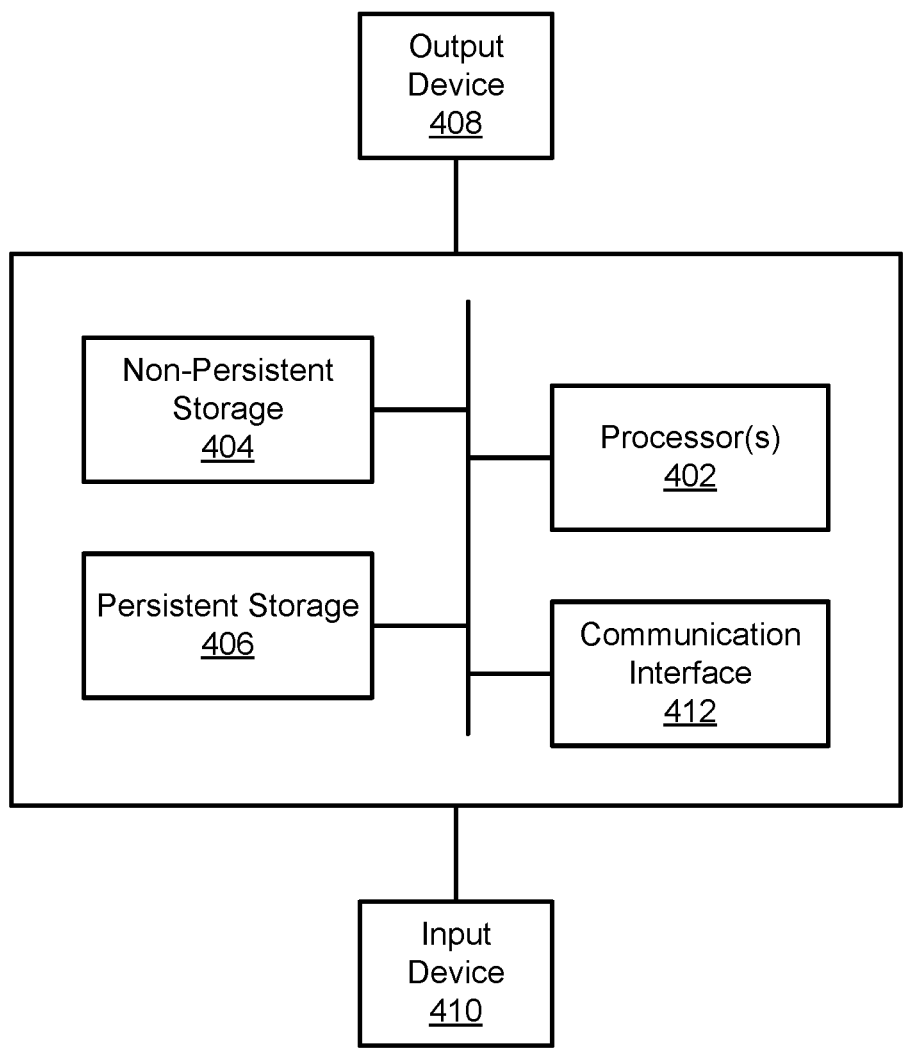
FIG. 4 shows a diagram of a computing device in accordance with one or more embodiments of the invention.

In one or more embodiments, the biomarker image generation service (150) may be implemented as a computing device (e.g., 400, FIG. 4). The computing device may be, for example, a mobile phone, a tablet computer, a laptop computer, a desktop computer, a server, a distributed computing system, or a cloud resource. The computing device may include one or more processors, memory (e.g., RAM), and persistent storage (e.g., disk drives, SSDs, etc.). The computing device may include instructions, stored in the persistent storage, that when executed by the processor(s) of the computing device cause the computing device to perform the functionality of the biomarker image generation service (150) described throughout this application.

Alternatively, in one or more embodiments, the biomarker image generation service (150) may be implemented as a logical device. The logical device may utilize the computing resources of any number of computing devices to provide the functionality of the biomarker image generation service (150) described throughout this application.

In one or more embodiments of the invention, the prognosis system (130) includes functionality for processing images obtained from the biomarker image generation service (150). For example, the biomarker image generation service (150) generates the original biomarker images (134) that are transmitted to the prognosis system (130) to be stored (e.g., in memory or in persistent storage) and used for the cancer prognosis process discussed throughout this disclosure.

In one or more embodiments, the prognosis system includes an image processing manager (132) that performs the method of FIGS. 2.1-2.2 to perform the cancer prognosis process. For example, the image processing manager (132) may use the original biomarker images (134) to generate a set of prognosis generated images (136) in accordance with FIG. 2.1. The prognosis generated images may be stored in memory or in persistent storage without departing from the disclosure. Collectively, the original biomarker images (134) and the prognosis generated images (136) may be collectively referred to as a set of synthetic images. The image processing manager may perform the method of FIG. 2.2 to process the set of synthetic images to perform the cancer prognosis process. The image processing manager (132) may utilize the computer-implemented services provided by the prognosis system (130) to perform the cancer prognosis process.

In one or more embodiments, in order to provide computer-implemented services, the prognosis system (130) may include a collection of physical components (e.g., processing resources, storage/memory resources, networking resources, etc.) configured to perform operations of the prognosis system (130) and/or otherwise execute a collection of logical components (e.g., applications, virtualization resources, etc.) of the prognosis system (130).

In one or more embodiments, a processing resource (not shown) may refer to a measurable quantity of a processing-relevant resource type, which can be requested, allocated, and consumed. A processing-relevant resource type may encompass a physical device (i.e., hardware), a logical intelligence (i.e., software), or a combination thereof, which may provide processing or computing functionality and/or services. Examples of a processing-relevant resource type may include (but not limited to): a CPU, a graphical processing unit (GPU), a data processing unit (DPU), etc.

As used herein, a "CPU" may refer to an electronic circuitry that may execute operations specified by an application. A CPU may perform an operation based on the following three steps: (i) fetching instructions related to an operation from the storage/memory resources, (ii) analyzing the fetched instructions, and (iii) performing the operation based on the analysis. In one or more embodiments, an operation may be, for example (but not limited to): comparing numbers, performing a function, displaying a video, etc.

As used herein, a "GPU" may refer to an electronic circuitry that may provide parallel data processing capabilities to generate enhanced, real-time graphics and to perform accelerated computing tasks (which is particularly useful for machine learning (ML) operations). In one or more embodiments, a GPU may include, for example (but not limited to): a graphics memory controller, a video processing engine, a graphics and computation engine, etc.

As used herein, a "DPU" may refer to an electronic circuitry that may perform accelerated data processing and optimized data movement data within each node. In one or more embodiments, the DPU may include, for example (but not limited to): a high-speed (e.g., 200 gigabits per second (200 Gbps)) networking interface, dynamic RAM (DRAM), a multi-core (e.g., 8-core) CPU, programmable acceleration engines (particularly for ML, security, and telecommunications purposes), etc.

In one or more embodiments, a storage or memory resource (not shown) may refer to a measurable quantity of a storage/memory-relevant resource type, which can be requested, allocated, and consumed. A storage/memory-relevant resource type may encompass a physical device, a logical intelligence, or a combination thereof, which may provide temporary or permanent data storage functionality and/or services. Examples of a storage/memory-relevant resource type may be (but not limited to): a hard disk drive (HDD), a solid-state drive (SSD), random access memory (RAM), Flash memory, a tape drive, a fibre-channel (FC) based storage device, a floppy disk, a diskette, a compact disc (CD), a digital versatile disc (DVD), a non-volatile memory express (NVMe) device, a NVMe over Fabrics (NVMe-oF) device, resistive RAM (ReRAM), persistent memory (PMEM), virtualized storage, virtualized memory, etc.

As used herein, "storage" may refer to a hardware component that is used to store data (e.g., application data) in each node. Storage may be a physical computer readable medium. In most cases, storage may be configured as a storage array (e.g., a network attached storage array), in which a storage array may refer to a collection of one or more physical storage devices. Each physical storage device may include non-transitory computer readable storage media, in which the data may be stored in whole or in part, and temporarily or permanently.

As used herein, "memory" may be any hardware component that is used to store data in each node. The data stored may be accessed almost instantly (e.g., in milliseconds (ms)) regardless of where the data is stored in memory. The memory may provide the above-mentioned instant data access because the memory may be directly connected to a CPU on a wide and fast bus (e.g., a high-speed internal connection that transfers data among hardware components of the node).

In one or more embodiments, the prognosis system (130) may be implemented as a computing device (e.g., 400, FIG. 4). The computing device may be, for example, a mobile phone, a tablet computer, a laptop computer, a desktop computer, a server, a distributed computing system, or a cloud resource. The computing device may include one or more processors, memory (e.g., RAM), and persistent storage (e.g., disk drives, SSDs, etc.). The computing device may include instructions, stored in the persistent storage that, when executed by the processor(s) of the computing device cause the computing device to perform the functionality of the prognosis system (130) described throughout this application.

Alternatively, in one or more embodiments, similar to the biomarker image generation service (150), the prognosis system (130) may also be implemented as a logical device.

While the system (100) illustrates only one biomarker image generation service (150), the prognosis system (130) may further include functionality for providing services associated with two or more biomarker image generation services without departing from the invention. In such embodiments in which the prognosis system (130) provides such services, the prognosis system (130) may store the original biomarker images (134) from the two or more biomarker image generation services.

In one or more embodiments, the clients (110) may provide computer-implemented services to users of the clients (110) (and/or other computing devices such as, other clients or other types of devices). The clients (110) may provide any number and any type of computer-implemented services (e.g., data storage services, electronic communication services, etc.). The clients (110) may be physical or logical devices, as discussed throughout this disclosure.

In one or more embodiments, the clients (110) may be implemented as computing devices (e.g., 400, FIG. 4). A computing device may be, for example, a mobile phone, a tablet computer, a laptop computer, a desktop computer, a server, a distributed computing system, or a cloud resource. The computing device may include one or more processors, memory (e.g., RAM), and persistent storage (e.g., disk drives, SSDs, etc.). The computing device may include instructions, stored in the persistent storage, that when executed by the processor(s) of the computing device cause the computing device to perform the functionality of the clients (110) described throughout this application.

Alternatively, in one or more embodiments, similar to the biomarker image generation service (150), the clients (110) may also be implemented as logical devices.

In one or more embodiments, the network (120) may represent a computing network configured for computing resource and/or messages exchange among registered computing hosts (i.e., the prognosis system (130), the biomarker image generation service (150), the clients (110), etc.). As discussed above, components of the system (100) may operatively connect to one another through the network (120) (e.g., a local area network (LAN), a wide area network (WAN), a mobile network, a wireless LAN (WLAN), etc.). In one or more embodiments, the network (120) may be implemented using any combination of wired and/or wireless connections. Further, the network (120) may enable interactions between the prognosis system (130), the biomarker image generation service (150), and the clients (110) through any combination of wired and/or wireless network protocols (e.g., TCP, UDP, Internet Protocol version 4 (IPv4), etc.).

The network (120) may encompass various interconnected, network-enabled subcomponents (not shown) (e.g., switches, routers, gateways, cables etc.) that may facilitate communications between the components of the system (100).

In one or more embodiments, the network-enabled subcomponents may be capable of: (i) performing one or more communication schemes (e.g., IP communications, Ethernet communications, etc.), (ii) being configured by one or more nodes (e.g., 130, 150, etc.) in the network (120), and (iii) limiting communication(s) on a granular level (e.g., on a per-port level, on a per-sending device level, etc.).

In one or more embodiments, before communicating data over the network (120), the data may first be broken into smaller batches (e.g., data packets) so that larger size data can be communicated efficiently. For this reason, the network-enabled subcomponents may break data into data packets. The network-enabled subcomponents may then route each data packet in the network (120) to distribute the network traffic uniformly.

FIG. 2.1 shows a flowchart of a method for generating a set of synthetic images in accordance with one or more embodiments of the invention. While various steps in the method are presented and described sequentially, those skilled in the art will appreciate that some or all of the steps may be executed in different orders, may be combined or omitted, and some or all steps may be executed in parallel without departing from the scope of the invention.

Turning now to FIG. 2.1, the method shown in FIG. 2.1 may be executed by, for example, the above-discussed image processing manager (132, FIG. 1). Other components of the system (100) illustrated in FIG. 1 may also execute all or part of the method shown in FIG. 2.1 without departing from the scope of the invention.

Turning to FIG. 2.1, in step 200, a set of original biomarker images are obtained from a biomarker image generation service. In one or more embodiments, the set of original biomarker images are obtained in response to a request sent by the prognosis system for the set of biomarker images. As an alternative, the set of original biomarker images are obtained in response to an initiated request by a client.

In step 202, the original biomarker images are divided based on protein channels to obtain divided biomarker images. In one or more embodiments, the original biomarker images may each include cells with multiple protein channels. The original biomarker images may be divided such that each of the divided biomarker images displays one of the protein channels for a corresponding set of tissue cells.

In step 204, image augmentation techniques are applied to the set of divided images to obtain a set of augmented images. In one or more embodiments, an image augmentation technique is a process for modifying a divided image to obtain one or more augmented image, each associated with the divided image. For example, a modification includes scaling, flipping, and rotating the divided image. In this example, performing a scaling of the divided image generates a first augmented image; performing a flipping of the divided image generates a second augmented image; and performing a rotation of the divided image generates a third augmented image. The divided image may be considered as the fourth augmented image without departing from the invention.

In step 206, one or more generative adversarial networks (GANs) model is applied to the set of augmented images to obtain a set of synthetic images. In one or more embodiments, a GAN is a machine learning algorithm for generating a set of images, each intended to be indistinguishable from an input set of images. For example, the GANs may include an image generative component that generates modified versions of the augmented images, and a discriminating component that determines whether an image is associated with an original image (e.g., an augmented image), or a modified image. An iteration of images is generated until the discriminating component has similar to a 50% rate of success for classifying the modified images. Said another way, in an iteration in which the discriminating component can correctly classify the modified images as modified with a 50% accuracy, the iteration of modified images are included in the set of synthetic images. The set of synthetic images may collectively comprise the modified images generated using the GANs, the set of divided images, and the set of augmented images.

In one or more embodiments, the method may end following step 206.

FIG. 2.2 shows a flowchart of a method for performing a prognosis using the set of synthetic images in accordance with one or more embodiments of the invention. While various steps in the method are presented and described sequentially, those skilled in the art will appreciate that some or all of the steps may be executed in different orders, may be combined or omitted, and some or all steps may be executed in parallel without departing from the scope of the invention.

Turning now to FIG. 2.2, the method shown in FIG. 2.2 may be executed by, for example, the above-discussed prognosis system (130, FIG. 1). Other components of the system (100) illustrated in FIG. 1 may also execute all or part of the method shown in FIG. 2.2 without departing from the scope of the invention.

In step 220, a grayscale is applied on the set of synthetic images to obtain a set of grayscale images. In one or more embodiments, the grayscale applied to a synthetic image includes setting the color of each pixel in the synthetic image to a monochromatic format. The monochromatic format may be a scale of gray to be assigned based on the original color of the pixel. The pixels may be represented numerically using a range of, e.g., 0 to 100. In this example, pixels with a numerical value of 0 may be illustrated using a black color, pixels with a numerical value of 100 may be illustrated using a white color, and pixels with an intermediate number may be illustrated using a gray color based on the gradient between white and black and the relative value of the intermediate number in the range.

In step 222, an entropy calculation is performed on each pixel of each grayscale image to obtain a set of entropy images. In one or more embodiments of the invention, the entropy calculation includes assigning an entropy value to each pixel of an image based on a calculated entropy of the pixel. The entropy may be calculated by identifying an entropy disk size (i.e., based on a pre-defined value of an administrator of the prognosis system), and comparing the changes in the pixels within the disk size of each pixel. In an image, the local entropy is related to the complexity contained in a given neighborhood of pixels, typically defined by a structuring element. An entropy filter can detect subtle variations in the local gray level distribution (e.g., within the entropy disk size).

In step 224, an entropy thresholding is performed on the set of entropy images to obtain a set of threshold images. In one or more embodiments, the entropy thresholding includes modifying each pixel based on an entropy threshold value. For example, each pixel with a numerical value that is below the entropy threshold value is modified to a setting of 0 (e.g., a black pixel). In this example, pixels with numerical values above the entropy threshold value may not be modified. The entropy threshold value may be a pre-defined value determined by an administrator of the prognosis system. In one or more embodiments, each entropy image may be associated with an entropy threshold value.

In step 226, a masking is performed on the set of threshold images to obtain a pair of masked images for each threshold image. In one or more embodiments, the masking performed on a threshold image includes generating a first masked image of a pair of masked images by modifying each pixel in the threshold image that is above a cancer threshold value (CTV). Any pixel below the CTV is not modified for the first masked image. Further, a second masked image of the pair of masked images is generated by modifying each pixel in the pair of threshold images that is below the CTV. Any pixel above the CTV is not modified for the second masked image.

In one or more embodiments, the pair of masked images is generated by inputting each threshold image to a pre-trained machine vision model (e.g., a pre-trained convolution neural network (CNN) machine learning model such as VGG16 model) to output two vector representations for each threshold image. The two vector representations of a threshold image may be referred to as a pair of masked images for the threshold image.

In step 228, each pair of masked images is compared using a cosine similarity value to assign a cancer prognosis to the pair of masked images. In one or more embodiments, after the two masked images in the pair of masked images are generated, the masked images are compared by first assigning a cosine similarity (CS) value to be used for the comparison. In one or more embodiments, the CS value is a numerical value, predetermined by the administrator, that measures the similarity of two vectors. The two vectors may be the pair of masked images for a threshold image. The cosine similarity may include measuring an angle of the two vectors in a domain and determining an angle between the two vectors. If the angle (i.e., the cosine value) is within a range of the CS value, the pair of masked images is considered similar; otherwise, the pair of masked images is considered non-similar. Those pairs of masked images that are similar are assigned as "non-cancerous", and those pairs of masked images that are not similar are assigned as "cancerous".

In step 230, a cancer prognosis is determined on each of the original biomarker images based on the cancer prognosis of each of the pair of masked images. In one or more embodiments, the threshold images are assigned a cancer prognosis in accordance with the assignment of their corresponding pair of masked images (e.g., "cancerous" or "non-cancerous"). The threshold image may be associated with an original biomarker image. One or more threshold images may be associated with the original biomarker image. Each of the one or more threshold images may be assigned a cancer prognosis. Based on the cancer prognoses of the one or more threshold images, a cancer prognosis is determined on the original biomarker image. For example, if any of the one or more threshold images associated with an original biomarker image is assigned a "cancerous" prognosis, the original biomarker image is also assigned a "cancerous" prognosis. Each original biomarker image may be assigned a cancer prognosis based on the cancer prognoses of the corresponding threshold image(s).

Example

FIGS. 3.1-3.5 show a non-limiting example in accordance with one or more embodiments disclosed herein. Turning to the example, consider a scenario in which a limited set of biomarker images are obtained from a biomarker image generation service (not shown). FIG. 3.1 shows a portion of the set of the obtained biomarker images. These may also be referred to as original biomarker images. Not all images obtained from the biomarker image generation service are illustrated in FIG. 3.1.

A prognosis system (not shown) performs the method of FIG. 2.1 to generate a set of synthetic images. Specifically, image augmentation techniques are applied to the set of original images to obtain augmented images. At least a portion of the set of augmented images is illustrated in FIG. 3.2. Further, a set of generative adversarial networks (GANs) are applied to the set of augmented images to generate a new set of images. Specifically, the new set of images include a set of virtually generated images (e.g., using artificial intelligence) and a portion of the augmented images that are applied to a machine learning algorithm to result in a set of synthetic images that include a combination of original images, augmented images, and virtually generated images such that each synthetic image may be substantially indistinguishable to a discriminating engine.

FIG. 3.3 shows a diagram of a synthetic image for a biomarker that includes non-cancerous cells. Conversely, FIG. 3.4 shows a synthetic image for a biomarker that indicates cancerous cells.

In this example, the prognosis system applies the method of FIG. 2.2 to the image of FIG. 3.3. Specifically, an entropy calculation is applied to each pixel of the image of FIG. 3.3. In this example, an entropy disk radius of 6 is applied to the image. Further, a scaled entropy image is generated by adjusting each pixel based on a ratio of the entropy value and a maximum value of the entropy values. Using the scaled entropy image, a set of threshold plots are generated. Each threshold plot is generated by setting, for each pixel in the scaled entropy image, the value of the pixel to 0 if the pixel is associated with a value that is below a predefined threshold. Nine threshold plots for multiple threshold values are illustrated in FIG. 3.5. Specifically, the top left-most threshold plot in FIG. 3.5 is associated with a threshold value of 0.1, and the bottom right-most threshold plot is associated with a threshold value of 0.9. Each intermediate threshold plot is associated with an intermediate threshold value.

Continuing the discussion of the example, the threshold plots are performed on each of the synthetic images as discussed above to generate threshold images. Further, after the threshold plots are performed, a pair of masked images are generated for each of the threshold images. The pair of masked images are performed by selecting a cancer threshold value, in accordance with FIG. 2.2, of 0.8 and applying a masking using the selected CTV. In this example, a mask image for pixels at or above the CTV make up a first masked image, and a mask image for pixels below the CTV make up a second image.

In this example, one of the threshold images in FIG. 3.5 is selected for illustrating a pair of masked images. FIGS. 3.6 shows an image of the first masked image (i.e., a masked image with pixels at or above the CTV that are modified). FIG. 3.7 shows an image of the second masked image (i.e., a masked image with pixels below the CTV modified). Using the images of FIGS. 3.6 and 3.7, a cosine similarity (CS) is performed in accordance with FIG. 2.2. In this example, the CS threshold used is 0.7. Based on the CS performed on the masked images, it is determined that the CS value of the two masked images is above the required CS threshold. Based on this, the associated image is determined to be non-cancerous.

End of Example

Turning now to FIG. 4, FIG. 4 shows a diagram of a computing device in accordance with one or more embodiments of the invention.

In one or more embodiments of the invention, the computing device (400) may include one or more computer processors (402), non-persistent storage (404) (e.g., volatile memory, such as RAM, cache memory), persistent storage (406) (e.g., a hard disk, an optical drive such as a CD drive or a DVD drive, a Flash memory, etc.), a communication interface (412) (e.g., Bluetooth interface, infrared interface, network interface, optical interface, etc.), an input device(s) (410), an output device(s) (408), and numerous other elements (not shown) and functionalities. Each of these components is described below.

In one or more embodiments, the computer processor(s) (402) may be an integrated circuit for processing instructions. For example, the computer processor(s) (402) may be one or more cores or micro-cores of a processor. The computing device (400) may also include one or more input devices (410), such as a touchscreen, keyboard, mouse, microphone, touchpad, electronic pen, or any other type of input device. Further, the communication interface (412) may include an integrated circuit for connecting the computing device (400) to a network (e.g., a LAN, a WAN, Internet, mobile network, etc.) and/or to another device, such as another computing device.

In one or more embodiments, the computing device (400) may include one or more output devices (408), such as a screen (e.g., a liquid crystal display (LCD), plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (402), non-persistent storage (404), and persistent storage (406). Many different types of computing devices exist, and the aforementioned input and output device(s) may take other forms.

Cancer research institutes and pharmaceutical companies that use biomarkers for the diagnosis for cancer treatments spend lot of money and time getting this data. Embodiments disclosed herein provide a unique application of GAN and image entropy in the cancer treatment domain which helps them in solving this problem in a cost effective and timely manner. Novel aspects of the invention include, but are not limited to: (i) using the concept of image entropy along with a cancer threshold value (CTV) of pixels. Transformation of image to a mask below and above CTV and then comparing the pair of masked images using cosine similarity may indicate the extent of regularity of the image which helps in determining if its cancerous or not, and (ii) using GAN model on augmented image dataset to generate more images of biomarkers. The GAN model can be fine-tuned to generate new samples of a particular type in order to generate more images in individual cases, and (iii) this technique based on entropy and mask above and below the CTV can be applied with slight modifications for various types of cancers. For example, in case of follicular cancers the image of a cancerous cell is regular (compared to other types of cancers) but still less regular than a non-cancerous cell and it can be identified using embodiments disclosed herein.

The problems discussed throughout this application should be understood as being examples of problems solved by embodiments described herein, and the various embodiments should not be limited to solving the same/similar problems. The disclosed embodiments are broadly applicable to address a range of problems beyond those discussed herein.

While embodiments discussed herein have been described with respect to a limited number of embodiments, those skilled in the art, having the benefit of this Detailed Description, will appreciate that other embodiments can be devised which do not depart from the scope of embodiments as disclosed herein. Accordingly, the scope of embodiments described herein should be limited only by the attached claims.

What is claimed is:

1. A system, comprising:
   a prognosis system, comprising hardware, programmed to:
      obtain, from a biomarker image generation service, a set of original biomarker images;
      generate a set of synthetic images using the set of original biomarker images;

perform an entropy calculation on each of the set of synthetic images to obtain a set of entropy images;

apply an entropy thresholding on the set of entropy images to obtain a set of threshold images;

apply a masking on the set of threshold images to obtain a pair of masked images for each of the set of threshold images;

compare each of the pair of masked images using a cosine similarity (CS) value to assign a cancer value to a corresponding threshold image of the set of threshold images; and based on the cancer value, determine a cancer prognosis to each of the synthetic images.

2. The system of claim 1, wherein generating the set of synthetic images comprises:

dividing each of the set of biomarker original images based on protein channels illustrated in each of the set of biomarker original images to obtain a set of divided biomarker images;

applying an image augmentation technique on each of the set of divided biomarker images to obtain a set of augmented images; and applying a generative adversarial network (GAN) algorithm on the set of augmented images to obtain the set of synthetic images.

3. The system of claim 2, wherein the set of synthetic images comprises the set of divided biomarker images, the set of augmented images, and a set of GAN-generated images.

4. The system of claim 1, wherein performing the entropy calculation on each of the set of synthetic images comprises:

identifying an entropy disk size; and assigning an entropy value to each pixel of a synthetic image of the set of synthetic images based on the entropy disk size to obtain an entropy image of the entropy images.

5. The system of claim 4, wherein applying the entropy thresholding comprises:

modifying each pixel of the entropy image that is below a first entropy threshold value to generate a first threshold image of the set of threshold images;

modifying each pixel of the entropy image that is below a second entropy threshold value to generate a second threshold image of the set of threshold images.

6. The system of claim 5, wherein applying the masking on the set of threshold images comprises:

modifying each pixel of the first threshold image that is below a cancer threshold value (CTV) to generate a first of a pair of masked images;

modifying each pixel of the first threshold image that is above a cancer threshold value (CTV) to generate a second of the pair of masked images.

7. The system of claim 6, wherein the cosine similarity value of the pair of masked images is below a CS threshold, and wherein the cancer prognosis indicates that a synthetic image associated with the pair of masked images is for cancerous cells.

8. The system of claim 6, wherein the cosine similarity value of the pair of masked images is above a CS threshold, and wherein the cancer prognosis indicates that a synthetic image associated with the pair of masked images is for non-cancerous cells.

9. The system of claim 1, wherein one of the set of original biomarker images is generated by applying a biomarker testing on human tissue and capturing a plurality of pictures of the results of the biomarker testing.

10. A method for managing access to a biomarker image generation service, the method comprising:

obtaining, by a prognosis system and from a biomarker image generation service, a set of original biomarker images;

dividing each of the set of biomarker original images based on protein channels illustrated in each of the set of biomarker original images to obtain a set of divided biomarker images;

applying an image augmentation technique on each of the set of divided biomarker images to obtain a set of augmented images;

applying a generative adversarial network (GAN) algorithm on the set of augmented images to obtain the set of synthetic images;

performing an entropy calculation on each of the set of synthetic images to obtain a set of entropy images;

applying a masking on the set of entropy images to obtain a pair of masked images for each of the set of entropy images;

comparing each of the pair of masked images using a cosine similarity (CS) value to assign a cancer value to a corresponding entropy image of the set of entropy images; and based on the cancer value, determine a cancer prognosis to each of the synthetic images.

11. The method of claim 10, wherein performing the entropy calculation on each of the set of synthetic images comprises:

identifying an entropy disk size; and assigning an entropy value to each pixel of a synthetic image of the set of synthetic images based on the entropy disk size to obtain an entropy image of the entropy images.

12. The method of claim 11, wherein applying the masking on the set of entropy images comprises:

modifying each pixel of the first entropy image that is below a cancer threshold value (CTV) to generate a first of a pair of masked images;

modifying each pixel of the first entropy image that is above a cancer threshold value (CTV) to generate a second of the pair of masked images.

13. The method of claim 12, wherein the cosine similarity value of the pair of masked images is below a CS threshold, and wherein the cancer prognosis indicates that a synthetic image associated with the pair of masked images is for cancerous cells.

14. The method of claim 12, wherein the cosine similarity value of the pair of masked images is above a CS threshold, and wherein the cancer prognosis indicates that a synthetic image associated with the pair of masked images is for non-cancerous cells.

15. The method of claim 10, wherein one of the set of original biomarker images is generated by applying a biomarker testing on human tissue and capturing a plurality of pictures of the results of the biomarker testing.

16. A non-transitory computer readable medium comprising computer readable program code, which, when executed by a computer processor, enables the computer processor to perform a method for managing access to a biomarker image generation service, the method comprising:

obtaining, by a prognosis system and from a biomarker image generation service, a set of original biomarker images;

dividing each of the set of biomarker original images based on protein channels illustrated in each of the set of biomarker original images to obtain a set of divided biomarker images;
applying an image augmentation technique on each of the set of divided biomarker images to obtain a set of augmented images;
applying a generative adversarial network (GAN) algorithm on the set of augmented images to obtain the set of synthetic images;
performing an entropy calculation on each of the set of synthetic images to obtain a set of entropy images;
applying a masking on the set of entropy images to obtain a pair of masked images for each of the set of entropy images;
comparing each of the pair of masked images using a cosine similarity (CS) value to assign a cancer value to a corresponding entropy image of the set of entropy images; and
based on the cancer value, determine a cancer prognosis to each of the synthetic images.

17. The non-transitory computer readable medium of claim 16, wherein performing the entropy calculation on each of the set of synthetic images comprises:
identifying an entropy disk size; and
assigning an entropy value to each pixel of a synthetic image of the set of synthetic images based on the entropy disk size to obtain an entropy image of the entropy images.

18. The non-transitory computer readable medium of claim 16, wherein applying the masking on the set of entropy images comprises:
modifying each pixel of the first entropy image that is below a cancer threshold value (CTV) to generate a first of a pair of masked images;
modifying each pixel of the first entropy image that is above a cancer threshold value (CTV) to generate a second of the pair of masked images.

19. The non-transitory computer readable medium of claim 18, wherein the cosine similarity value of the pair of masked images is below a CS threshold, and wherein the cancer prognosis indicates that a synthetic image associated with the pair of masked images is for cancerous cells.

20. The non-transitory computer readable medium of claim 18, wherein the cosine similarity value of the pair of masked images is above a CS threshold, and wherein the cancer prognosis indicates that a synthetic image associated with the pair of masked images is for non-cancerous cells.

* * * * *